United States Patent
Kaus

(12) 
(10) Patent No.: US 6,327,716 B1
(45) Date of Patent: Dec. 11, 2001

(54) URINAL CONE AND PACKAGING THEREFOR

(76) Inventor: Reinhold Kaus, Parkstrasse 6, D-65439 Flörsheim (DE)

( * ) Notice: Subject to any disclaimer, the term of this patent is extended or adjusted under 35 U.S.C. 154(b) by 0 days.

(21) Appl. No.: 09/171,613

(22) PCT Filed: Apr. 22, 1996

(86) PCT No.: PCT/EP96/01674

§ 371 Date: Oct. 22, 1998

§ 102(e) Date: Oct. 22, 1998

(87) PCT Pub. No.: WO97/39706

PCT Pub. Date: Oct. 30, 1997

(51) Int. Cl.⁷ .................................................. A47K 11/12
(52) U.S. Cl. ................................................................ 4/144.4
(58) Field of Search ................................................ 4/144.4

(56) References Cited

U.S. PATENT DOCUMENTS 2,878,486 * 3/1959 Bartlett et al. ...................... 4/144.4
4,023,216    5/1977 Li ........................................ 4/144.4

FOREIGN PATENT DOCUMENTS 0158602  10/1985 (EP) .
0226277   6/1987 (EP) .
93/11691  6/1993 (WO) .

* cited by examiner

*Primary Examiner*—Robert M. Fetsuga
(74) *Attorney, Agent, or Firm*—Venable; Robert Kinberg; Catherine M. Voorhee

(57) ABSTRACT

A urinal cone, particularly for persons of the female gender, is to be applied to the genital area of the person for the purpose of urinating is described. The urinal cone is designed to permit a hygienic urinating of persons under unhygienic conditions or unfavorable conditions and, in addition, should be easily available, easy to handle and disposable following use. For this, the urinal cone can be set up from an essentially triangular shape in the collapsed state to form a funnel-shaped body, comprising an envelope having an upper opening of large diameter and an opposite-arranged lower opening of small diameter.

11 Claims, 2 Drawing Sheets

URINAL CONE AND PACKAGING THEREFOR

BACKGROUND OF THE INVENTION

The invention relates to a urinal cone, in particular for persons of the female gender, to be applied to the genital area of the person for the purpose of urinating, which urinal cone can be set up from an essentially triangular shape in the collapsed state to form a funnel-shaped body, comprising an envelope having an upper opening of large diameter and an opposite-positioned lower opening of small diameter.

Given unfavorable environmental conditions and circumstances, urinating frequently is a problem, particularly for persons of the female gender. Such unfavorable environmental conditions and circumstances often occur when a plurality of persons meet for events of any kind. In that case, bathrooms, public restrooms or similar hygienic facilities can become dirty even with less frequent use, such that subsequently arriving persons will feel too repulsed to take care of their needs in such bathrooms. Of necessity, this applies especially to persons of the female gender, since they must urinate while sitting down. Such a dirtying of restrooms can occur, for example, in public transportation means such as tour buses, trains, etc., which must be used over long periods of time.

Further unfavorable environmental conditions and circumstances result from the use of gutters or drainage holes in place of toilet bowls, e.g in countries with a different culture where. The use of such facilities in place of restrooms is strange and takes getting used to for persons coming from countries where toilet bowls are normally used. Also, the use of such bathroom facilities is frequently associated with a spattering of the discharged urinary fluid. In many cases, restroom facilities lack all traces of generally acceptable hygienic conditions.

A urinal cone with polygonal shape when in the collapsed state is disclosed in the reference U.S. Pat. No. 4,023,216. One end of the urinal cone has a bias cut opening of small diameter. An opening of large diameter is formed at the opposite end of the urinal cone, which has straight-line sections, pointing away from an adhesive fold at the envelope, which sections change to short, evenly extending curved sections, which again change to short straight-line sections that are connected by an also straight-line section. The upper urinal cone opening of large diameter thus is distinguished by a plurality of edges with a different course, which form a plurality of corner points.

The EP-A-0226277 discloses a urinal cone having an essentially triangular shape when collapsed and a lower opening of small diameter, as well as an upper opening of large diameter. The opening of large diameter is cut at an extreme angle, relative to the side edges of the urinal cone, and has an approximately straight-line cutting edge.

The WO 93/11691 discloses a urinal cone with a triangular shape in the collapsed state and a lower opening of small diameter as well as an upper opening of large diameter. In the collapsed state, the upper opening of large diameter has a curvature with an essentially unchanged radius.

SUMMARY OF THE INVENTION

Thus, it is the object of the invention to create a urinal cone, particularly for persons of the female gender, to be applied to the genital area of the person for the purpose of urinating. Such a cone is designed to allow persons to urinate hygienically under unhygienic or unfavorable conditions and should additionally be easily available, easy to use and easy to dispose of following the use.

This object is solved in accordance with the invention in that the outside contour of the envelope in the collapsed state of the urinal cone in the region of the upper opening of large diameter has a continuously tapered radius of curvature extending from one side to the other side of the essentially triangular envelope shape, with the sides extending respectively from the lower opening of small diameter, wherein the upper opening of the envelope can be applied to the genital area of the person in such a way that this area is enclosed tightly. In the flat state, the urinal cone is simply unfolded to form a funnel-shaped body. With its upper opening, this cone is applied to the genital area of the person, e.g. the vagina of a person of the female gender, such that the opening of small diameter is directed downward and produces a thin urinary stream during urination, which is diverted, for example, into a bathroom facility. Following use, the urinal cone is simply disposed of in a garbage container, e.g. folded up. The use of this urinal cone allows the respective person to urinate while standing, sitting or squatting, without coming into contact with the bathroom facility. Owing to the fact that the stream of urinary fluid is formed by the lower opening of small diameter, a spattering of the urinary fluid when leaving the urinal cone is avoided.

The continuously tapered radius of curvature of the upper urinal cone opening of large diameter ensures that when setting the urinal cone up from the collapsed state, it can be adapted to the body shape of the person using it, such that it encloses the genital area tightly. It is left up to the user to find the best place for applying the urinal cone to his/her body.

According to a modification of the invention in the collapsed state, the lower opening of small diameter is beveled. This measure changes the cross section of the urinary stream in such a way that a spattering of the urinary fluid is essentially avoided when it hits the ground.

It makes sense if the lower opening has a diameter of at least 5 mm and the upper opening has a diameter of at least 50 mm to ensure that the urinal cone functions well.

In addition, the urinal cone has an adhesive strip along the funnel-shaped envelope, which connects the upper opening of large diameter with the lower opening of small diameter. The one-piece envelope for the urinal cone comprises this adhesive strip so that it can be set up to form a funnel-shaped body. The adhesive strip preferably can be made to adhere to the funnel-shaped envelope. The envelope can furthermore be connected on at least one of its sides through reeding or the like, which is a method of joining the outer edges of an envelope such as a cone-shaped coffee filter, for example.

The funnel-shaped envelope has at least two folding lines, extending from the lower opening of small diameter to the upper opening of large diameter, so as to be able to transport the unused urinal cone, e.g. inside a handbag, wherein it should take up as little space as possible. The urinal cone can thus be folded along these folding lines, and its outside contour can be reduced.

In a preferred embodiment of the invention, the urinal cone is composed of paper or cardboard. Furthermore, at least one side of the paper or cardboard is preferably coated with wax. The urinal cone can also consist of foil, a foil-type material, particularly a water-proof material. This prevents the urinary fluid from softening and deforming the urinal cone.

The object of the invention is also solved with a packaging for the urinal cone, which accommodates a plurality of urinal in the collapsed state, wherein the outside contour of the packaging essentially corresponds to the urinal cone in the folded state. As a result, a plurality of urinal cones can be arranged one above the other in the packaging, either in the collapsed state or folded even further along the folding lines. Thus, a plurality of urinal cones can be placed inside one packaging, which can fit into any handbag or jacket pocket.

It makes sense if the packaging is also made of paper or cardboard, preferably a paper or cardboard with wax coating on one side. Furthermore, the packaging can also be made of a foil or foil-type material.

It is understood that the aforementioned as well as the following features, which are still to be explained, can be used not only in the respectively mentioned combination, but also in other combinations or by themselves, without leaving the scope of the present invention.

BRIEF DESCRIPTION OF THE DRAWINGS

The invention is described further in the following, with the aid of an exemplary embodiment and by referring to the associated drawings, wherein.

DETAILED DESCRIPTION OF THE INVENTION

Figure 1:
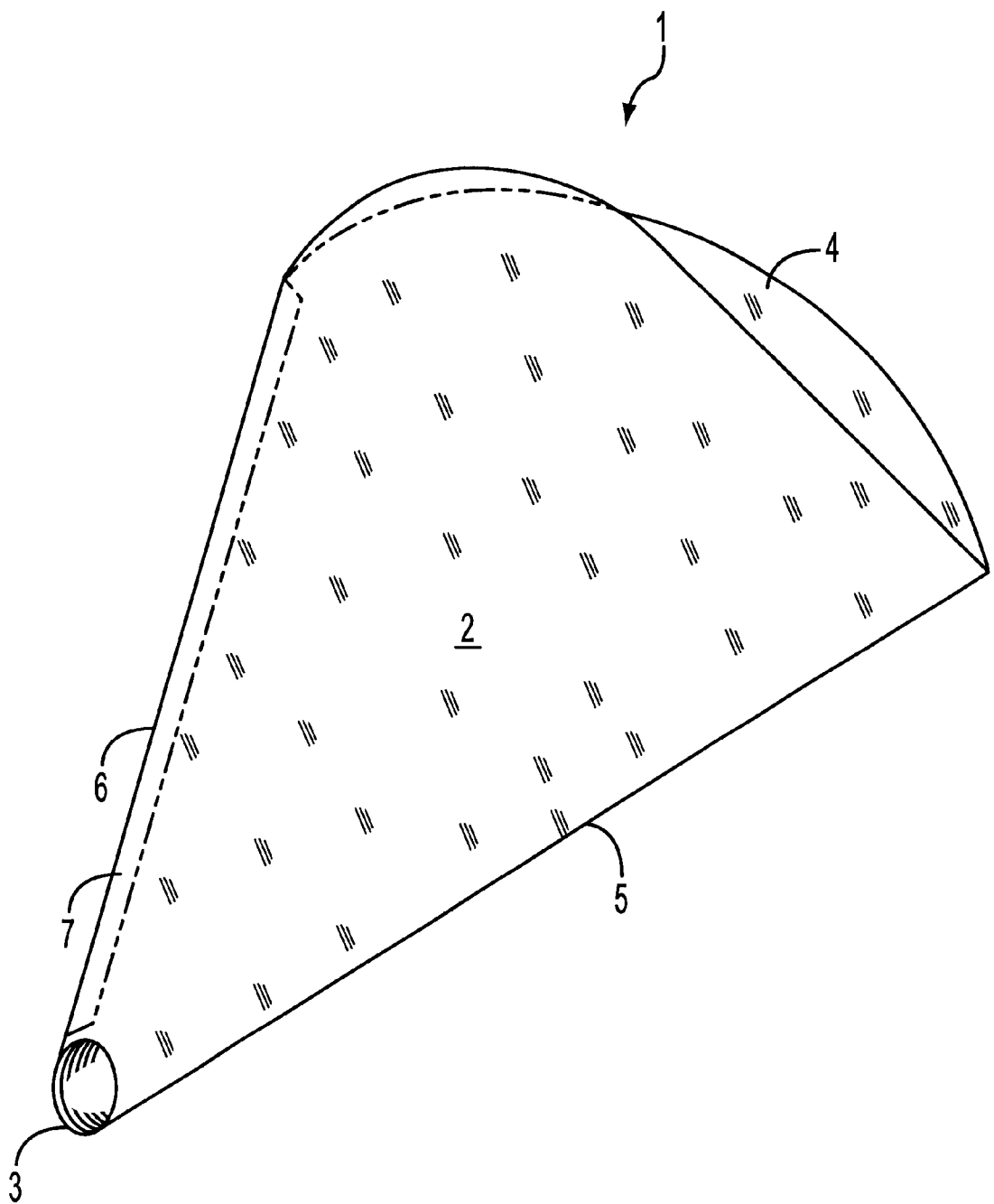
FIG. 1 Shows a perspective view of a urinal cone according to the invention.
Figures 2, 2A:
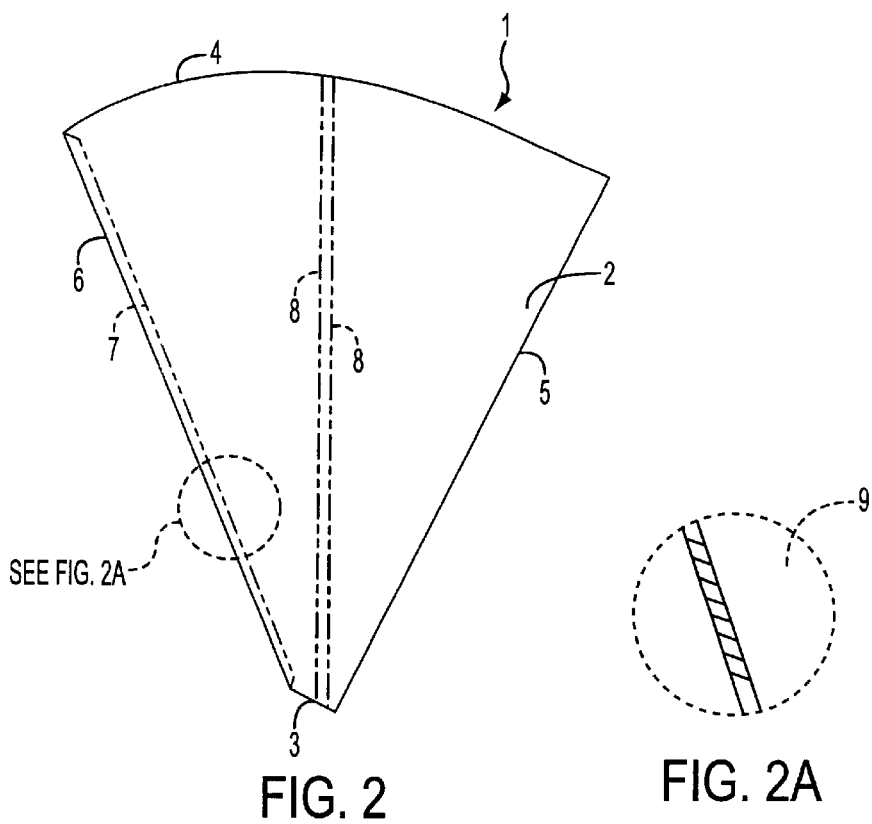
FIG. 2 Shows a side view of the urinal cone according to FIG. 1.
FIG. 2a shows a portion of a side of a urinal cone according to the invention where the sides of envelope 2 are connected through reeding.

In accordance with FIGS. 1 and 2, the collapsed urinal cone 1 according to the invention consists essentially of a funnel-shaped envelope 2, composed of paper or cardboard. The material strength should be particularly suited to change the urinal cone 1 from the collapsed state according to FIG. 2 to the set-up state according to FIG. 1. It makes sense if the inside as well as the outside of the material is provided with a coating of with wax to prevent the urinary fluid from soaking through. In addition, the material should not crease or deform in any way during the use of the urinal cone.

In the collapsed state according to FIG. 2, the funnel-shaped envelope 2 has an essentially triangular form. In the state in which the urinal cone 1 is set up according to FIG. 1, the funnel-shaped envelope 2 is essentially cone-shaped with the tip of the cone cut off. As a result, a lower opening 3 of small diameter is created, through which the urinary fluid is discharged. At the side of envelope 2 that is located opposite the lower opening 3 of small diameter, the envelope has an upper opening 4 of large diameter. As can be seen in particular in FIG. 2, the outside contour of funnel-shaped envelope 2 has a radius of curvature in the upper opening 4 region, which is tapered continuously from one side 5 to the other side 6 of the funnel-shaped envelope 2. The region with stronger curvature of the upper opening 4 of large diameter thus can be applied easier in the genital area between the legs of the user, so as to enclose the genital area tightly.

To obtain a funnel-shaped or cone-shaped design for the envelope 2, an adhesive strip 7 is integrated between the lower opening 3 of small diameter and the upper opening 4 of large diameter into envelope 2, along one side 6 of the funnel-shaped envelope 2. It makes sense if the outside of adhesive strip 7 is glued to the adjacent inside region of envelope 2 with a suitable adhesive.

Furthermore, a folding line is provided between the lower opening 3 of small diameter and the upper opening 4 of large diameter, represented by a dash-dot-dash line, around which the envelope 2 of urinal cone 1 can be folded to reduce its size by one half.

Alternatively, side 6 of envelope 2 can be connected through reeding 9 or the like. FIG. 2a shows a side portion A' similar to the side portion A of FIG. 2 where reeding 9 is schematically shown to connect sides 6 of envelope 2.

Figure 3:
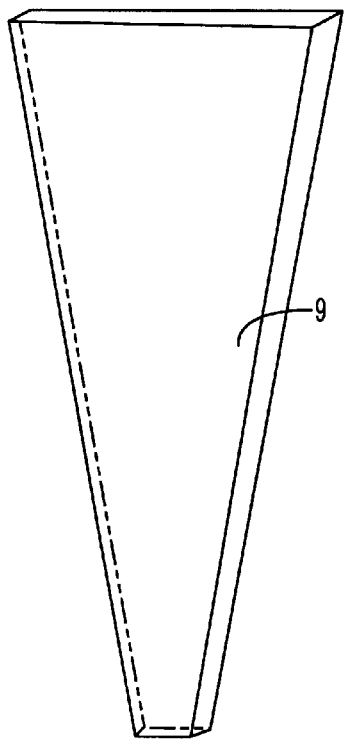
FIG. 3 Shows a packaging to accommodate a plurality of urinal cones according to the FIGS. 1 and 2.

FIG. 3 shows a packaging 9 for a plurality of urinal cones 1, the contour of which corresponds to a urinal cone according to FIG. 2 if this cone is folded in the collapsed state around the folding line 8. Owing to its small dimensions, the packaging 9, which is reduced to half the size of urinal cone 1, can be stored inside a handbag or jacket pocket to protect the urinal cone against damaging influences, such as dirt or moisture.

What I claim is:

1. A urinal cone, particularly for a person of the female gender, to apply to the genital region of the person for the purpose of urinating, which urinal cone can be set up from an essentially triangular shape to form a funnel-shaped body, comprising an envelope with an upper opening of a large diameter and an opposite-positioned lower opening of a small diameter wherein the outside contour of the upper opening has a continuously tapered radius of curvature and the upper opening of the envelope can be applied to the genital area of the person in such a way that this area is enclosed tightly in order for the person to urinate in a variety of positions including sitting, standing and squatting.

2. A urinal cone according to claim 1, wherein in the collapsed state of the urinal cone, the lower opening of small diameter is beveled.

3. A urinal cone according to claim 1, wherein the lower opening has a diameter of at least 5 mm.

4. A urinal cone according to claim 1 wherein the upper opening has a diameter of at least 50 mm.

5. A urinal cone according to claim 1, wherein it has an adhesive strip that connects the upper opening of large diameter with the lower opening of small diameter along the funnel-shaped envelope.

6. A urinal cone according to claim 1, wherein the adhesive strip can be glued to the funnel-shaped envelope.

7. A urinal cone according to claim 1, wherein the envelope is connected on at least one of its sides through reeding or the like.

8. A urinal cone according to claim 1, wherein the funnel-shaped envelope has at least two folding line that extend from the lower opening of small diameter to the upper opening of large diameter.

9. A urinal cone according to claim 1, wherein the urinal fluid can be discharged through the opening of small diameter in the envelope.

10. A urinal cone according to claim 1, wherein said cone consists of paper or cardboard.

11. A urinal cone according to claim 1, wherein said cone consists of a foil, a foil-type material, in particular a waterproof material.

* * * * *

UNITED STATES PATENT AND TRADEMARK OFFICE
CERTIFICATE OF CORRECTION

PATENT NO. : 6,327,716 B1  
DATED : December 11, 2001  
INVENTOR(S) : Kaus

It is certified that error appears in the above-identified patent and that said Letters Patent is hereby corrected as shown below:

<u>Title page,</u>
Insert -- [*] Notice: Under 35 U.S.C. 154(b), the term of this patent shall be extended for 480 days. --.

Signed and Sealed this

Third Day of December, 2002

JAMES E. ROGAN
*Director of the United States Patent and Trademark Office*